(12) United States Patent
Hoffman

(10) Patent No.: US 12,364,676 B2
(45) Date of Patent: Jul. 22, 2025

(54) COMPOSITIONS AND METHODS FOR TREATING RETINOPATHY

(71) Applicant: Yamo Pharmaceuticals LLC, New York, NY (US)

(72) Inventor: Steven Hoffman, Mahwah, NJ (US)

(73) Assignee: YAMO PHARMACEUTICALS LLC, New York, NY (US)

( * ) Notice: Subject to any disclaimer, the term of this patent is extended or adjusted under 35 U.S.C. 154(b) by 653 days.

(21) Appl. No.: 17/830,458

(22) Filed: Jun. 2, 2022

(65) Prior Publication Data

US 2022/0288003 A1 Sep. 15, 2022

Related U.S. Application Data

(62) Division of application No. 15/958,598, filed on Apr. 20, 2018, now Pat. No. 11,351,136.

(60) Provisional application No. 62/488,161, filed on Apr. 21, 2017.

(51) Int. Cl.
| | |
|---|---|
| *A61K 31/198* | (2006.01) |
| *A61K 9/00* | (2006.01) |
| *A61K 31/20* | (2006.01) |
| *A61K 31/201* | (2006.01) |
| *A61K 31/4166* | (2006.01) |
| *A61K 31/55* | (2006.01) |
| *A61K 45/06* | (2006.01) |
| *A61K 47/10* | (2017.01) |
| *A61K 47/12* | (2006.01) |
| *A61P 27/02* | (2006.01) |

(52) U.S. Cl.
CPC .......... *A61K 31/198* (2013.01); *A61K 9/0014* (2013.01); *A61K 31/20* (2013.01); *A61K 31/201* (2013.01); *A61K 31/55* (2013.01); *A61K 45/06* (2013.01); *A61K 47/10* (2013.01); *A61K 47/12* (2013.01); *A61P 27/02* (2018.01); *A61K 31/4166* (2013.01); *A61K 2300/00* (2013.01)

(58) Field of Classification Search
None
See application file for complete search history.

(56) References Cited

U.S. PATENT DOCUMENTS

| | | |
|---|---|---|
| 2014/0128460 A1 | 5/2014 | Hedge |
| 2015/0111878 A1 | 4/2015 | Hoffman |
| 2016/0199453 A1 | 7/2016 | Hoffman |

FOREIGN PATENT DOCUMENTS

WO  WO 2015/061288  4/2015

OTHER PUBLICATIONS

El-Asrar et al., The Proinflammatory Cytokine High-Mobility Group Box-1 Mediates Retinal Neuropathy Induced by Diabetes, 2014, Mediators of Inflammation, Article ID 746415, pp. 1-10.
Gao, S. S. et al. (Jul. 2016). "Optical Coherence Tomography Angiography", Investigative Ophthalmology & Visual Science 57(9): Oct. 27-Oct. 36.
Bhatia et al., "Catecholamines in Diabetic Retinopathy" Annals of Ophthalmology, vol. 15, No. 7, Jul. 1983, pp. 677-679.
Leitgeb, R. A. et al. (Jul. 2014). "Doppler Optical Coherence Tomography", Progress in Retinal and Eye Research 41 (100): 26-43.

*Primary Examiner* — Jeffrey S Lundgren
*Assistant Examiner* — Michael J Schmitt
(74) *Attorney, Agent, or Firm* — BakerHostetler

(57) ABSTRACT

The present invention provides methods, compositions, and kits for treating retinopathy, including diabetic retinopathy and macular degeneration, in a subject in need.

7 Claims, No Drawings

COMPOSITIONS AND METHODS FOR TREATING RETINOPATHY

CROSS-REFERENCE TO RELATED APPLICATIONS

This application is a divisional of U.S. patent application Ser. No. 15/958,598, filed Apr. 20, 2018, which claims the benefit of U.S. Provisional Patent Application No. 62/488,161, filed on Apr. 21, 2017. The entirety of each of the aforementioned applications is incorporated by reference herein.

TECHNICAL FIELD

The present inventions relate generally to compositions, kits, and methods for the treatment of retinopathy, including diabetic retinopathy and macular degeneration.

BACKGROUND

The retina is a layer of nerve cells that lines the back wall of the interior of the eyeball. The retina receives the light image formed by the lens and converts that image into signals which reach the brain by through the optic nerve. The macula, a small region in the center of the retina, enables the eye to distinguish fine details such as written text. Retinopathy is a general term that refers to disorders of the retina.

One type of retinopathy is diabetic retinopathy. High blood sugar levels in diabetics damages the blood vessels in the retina. This damage can result in swelling and leaking of the blood vessels, closing of the blood vessels to cut-off blood flow to the retina, and growth of abnormal blood vessels on the retina. Diabetic retinopathy generally proceeds in two stages. In the early stage of diabetic retinopathy, known as non-proliferative diabetic retinopathy, the blood vessels can swell and leak, causing macular edema. The blood vessels can also close off, causing macular ischemia. The advanced stage of diabetic retinopathy is called proliferative diabetic retinopathy. In this stage, the retina grows new blood vessels that can leak or form scar tissue. Diabetic retinopathy adversely affects the vison, ranging from blurred vision to vision loss.

Another type of retinopathy is macular degeneration. Macular degeneration results from damage to the macula and results in loss of central vision, including the ability to see fine details. Macular degeneration is often age-related, occurring as a natural part of the aging process.

There are two types of macular degeneration: dry macular degeneration and wet macular degeneration. The most common type of macular degeneration, dry macular degeneration, occurs when the macula thins with age and small protein deposits form under the retina. In wet macular degeneration, new, abnormal blood vessels grow under the retina and cause scarring of the macula.

The drugs currently available for treating diabetic retinopathy and macular degeneration include ranibizumab, bevacizumab, and aflibercept. These antibody-derived drugs are all administered by injection into the eye of the patient by the physician. Thus, there remains a need for additional effective treatments or cures for retinopathy, particularly those that can be administered by the patient.

SUMMARY

The present invention provides methods, compositions, and kits for treating retinopathy in a subject in need thereof, including diabetic retinopathy and macular degeneration. In certain embodiments, the invention provides methods comprising administering to a subject in need thereof an effective amount of a tyrosine hydroxylase inhibitor and a p450 3A4 promoter.

In other embodiments, the invention provides pharmaceutical compositions comprising a tyrosine hydroxylase inhibitor and a p450 3A4 promoter. Also provided are kits comprising a tyrosine hydroxylase inhibitor and a p450 3A4 promoter together with packaging for same.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment incudes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be retinopathy.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with respect to the particular compound, component or composition selected, the route of administration, and the ability of the components to elicit a desired result in the individual, but also with respect to factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"High blood glucose level" is used interchangeably with "hyperglycemia" herein and is defined as a fasting plasma blood glucose level of 126 mg/dl or greater on two separate occasions.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space. The term "enantiomers" refers to stereoisomers that are mirror images of each other that are non-superimposable.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

While not intending to be bound by any particular mechanism of operation, it is believed that the tyrosine hydroxylase inhibitors according to the present invention function by reducing activity of the adrenal system to reduce vasoconstriction and, in turn, increase blood flow to the retina.

Methods of treating retinopathy in a subject are provided. Such methods can include administering to a subject in need thereof an effective amount of a tyrosine hydroxylase inhibitor. Other such methods include administering to a subject in need thereof an effective amount of tyrosine hydroxylase inhibitor and a p450 3A4 promoter. This tyrosine hydroxylase inhibitor and the p450 3A4 promoter can be administered simultaneously.

Administration of the tyrosine hydroxylase inhibitor or the tyrosine hydroxylase inhibitor and the p450 3A4 promoter can be through various routes, including orally, nasally subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether. Preferred transdermal formulations are described in U.S. Published Application No. 2016-0199453, which is incorporated herein by reference.

In other suitable embodiments of the invention the tyrosine hydroxylase inhibitor and the p450 3A4 promoter are administered during a cycle consisting of five to seven days of administering the tyrosine hydroxylase inhibitor and the p450 3A4 promoter, and one to two days of not administering the tyrosine hydroxylase inhibitor and the p450 3A4 promoter. In some suitable embodiments of the invention, at least six of said cycles of administration are performed. In some suitable embodiments of the invention, 25 mg of the tyrosine hydroxylase inhibitor is administered.

In certain embodiments, the tyrosine hydroxylase inhibitor is a tyrosine derivative. The tyrosine derivative can be capable of existing in different isomeric forms, including stereoisomers and enantiomers. The tyrosine derivative can, for example, exist in both L-form or D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine methyl ester hydrochloride, H-3,5-diiodo-tyrosine methyl ester hydrochloride, H-D-3,5-diiodo-tyrosine methyl ester hydrochloride, H-D-tyrosine methyl ester hydrochloride, D-tyrosine methyl ester hydrochloride, D-tyrosine-methyl ester hydrochloride, methyl D-tyrosinate hydrochloride, H-D-tyrosine methyl ester•hydrochloride, D-tyrosine methyl ester hydrochloride, H-D-tyrosine methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other embodiments, the tyrosine derivative is α-methyl-D-tyrosine. In other embodiments, the tyrosine derivative is α-methyl-DL-tyrosine in a racemic form.

Representative p450 3A4 promoters include 5, 5-diphenylhydantoin, valproic acid and carbamazepine. In a suitable embodiment of the invention, the composition includes 5 mg to 25 mg of 5, 5-diphenylhydantoin. Representative subjects include mammals. In certain embodiments, the mammal is a human.

In some embodiments of the invention, methods further comprising assessing progression of said retinopathy in said subject are provided. This assessing step can be performed before said administering step or after said administering step.

Representative conditions that can be treated with methods of the present invention include retinopathy, including diabetic retinopathy, non-proliferative diabetic retinopathy, proliferative diabetic retinopathy, macular degeneration, dry macular degeneration, and wet macular degeneration.

Administration of pharmaceutically active molecules such as inhibitor and/or promoters can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, dodecylnonaoxyethylene glycol monoether.

The tyrosine hydroxylase inhibitor can be administered during a cycle consisting of five to seven days of administering the tyrosine hydroxylase inhibitor, and one to two days of not administering the tyrosine hydroxylase inhibitor. The tyrosine hydroxylase inhibitor can be administered over the course of at least six said cycles. In one suitable embodiment of the invention, the tyrosine hydroxylase inhibitor is administered daily. In another suitable embodiment of the invention, the tyrosine hydroxylase inhibitor is administered multiple times per day.

Representative treatment methods according to the invention comprise administering to a subject in need thereof an effective amount of a tyrosine hydroxylase inhibitor or a tyrosine hydroxylase inhibitor and a p450 3A4 promoter are provided.

Suitable embodiments can include a pharmaceutical composition comprising a tyrosine hydroxylase inhibitor and a p450 3A4 promoter. The tyrosine hydroxylase inhibitor can be a tyrosine derivative.

Also provided herein are kits comprising a tyrosine hydroxylase inhibitor and a p450 3A4 promoter together with packaging for same. The tyrosine hydroxylase inhibitor can be a tyrosine derivative. The tyrosine derivative can include tyrosine derivatives capable of existing in isomeric form. The tyrosine derivatives can include tyrosine derivatives in its L-form or in its D-form. The tyrosine derivative can, for example, also exist in a racemic form. Representative tyrosine derivatives include one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-tyrosine(tBu)-allyl ester hydrochloride, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyrosine-methyl ester hydrochloride, H-3,5-diiodo-tyrosine-methyl ester hydrochloride, H-D-3,5-diiodo-tyrosine-methyl ester hydrochloride, H-D-tyrosine-methyl ester hydrochloride, D-tyrosine methyl ester hydrochloride, D-tyrosine-ome hydrochloride, methyl D-tyrosinate hydrochloride, H-D-tyrosine-methyl ester•hydrochloride, D-tyrosine methyl ester hydrochloride, H-D-tyrosine-methyl ester-hydrochloride, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-tyrosine (3,5I2)-OSu, Fmoc-tyrosine(3-NO2)-OH, α-methyl-L-tyrosine, α-methyl-D-tyrosine, and α-methyl-DL-tyrosine. In certain embodiments of the invention, the tyrosine derivative is α-methyl-L-tyrosine. In other specific embodiments of the invention, the tyrosine derivative is α-methyl-D-tyrosine. In other embodiments, the tyrosine derivative is α-methyl-DL-tyrosine in a racemic form.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1—Diabetic Retinopathy 100 patients with diabetic retinopathy are divided into a control group (n=50) and a test group (n=50). The baseline retinal blood flow and vascularization in both groups is assessed using Doppler Optical Coherence Tomography and Optical Coherence Tomography Angioagraphy. *See*, e.g., Gao S S, et al. Optical Coherence Tomography Angiography, *Invest Ophthalmol Vis Sci.* 2016, 57:OCT27-OCT36; see also Leitgeb, R A et al., Doppler Optical Coherence Tomography, *Progress in Retinal and Eye Research* 2014, 41, 26-43. Patients in the test group are administered daily doses of tyrosine hydroxylase inhibitor. After 30 days, the retinal blood flow and retinal vasculature of both the control and test groups is again evaluated. The test group shows improved retinal blood flow and reduced abnormal retinal vasculature relative to the control group.

Example 2—Macular Degeneration 100 patients with macular degeneration are divided into a control group (n=50) and a test group (n=50). The baseline retinal blood flow and vascularization in both groups is assessed using Doppler Optical Coherence Tomography and Optical Coherence Tomography Angioagraphy. *See*, e.g., Gao S S, et al. Optical Coherence Tomography Angiography, *Invest Ophthalmol Vis Sci.* 2016, 57:OCT27-OCT36; see also Leitgeb, R A et al., Doppler Optical Coherence Tomography, *Progress in Retinal and Eye Research* 2014, 41, 26-43. Patients in the test group are administered daily doses of tyrosine hydroxylase inhibitor. After 30 days, the retinal blood flow and retinal vasculature of both the control and test groups is again evaluated. The test group shows improved retinal blood flow and reduced abnormal retinal vasculature relative to the control group.

What is claimed:
1. A method of treating macular degeneration in a subject comprising administering to a subject in need thereof an effective amount of α-methyl DL-tyrosine.
2. The method of claim 1 wherein the macular degeneration is wet macular degeneration.
3. The method of claim 1 wherein the macular degeneration is dry macular degeneration.
4. The method of claim 1, wherein the α-methyl DL-tyrosine is administered orally, subcutaneously, intravenously, transdermally, vaginally, rectally or in any combination thereof.
5. The method of claim 4, wherein the transdermal administration is performed in combination with oleic acid, 1-methyl-2-pyrrolidone, or dodecylnonaoxyethylene glycol monoether.
6. The method of claim 1, wherein the subject is a human.
7. The method of claim 1, further comprising assessing the progression of the macular degeneration in the subject.

* * * * *